Figure 4:
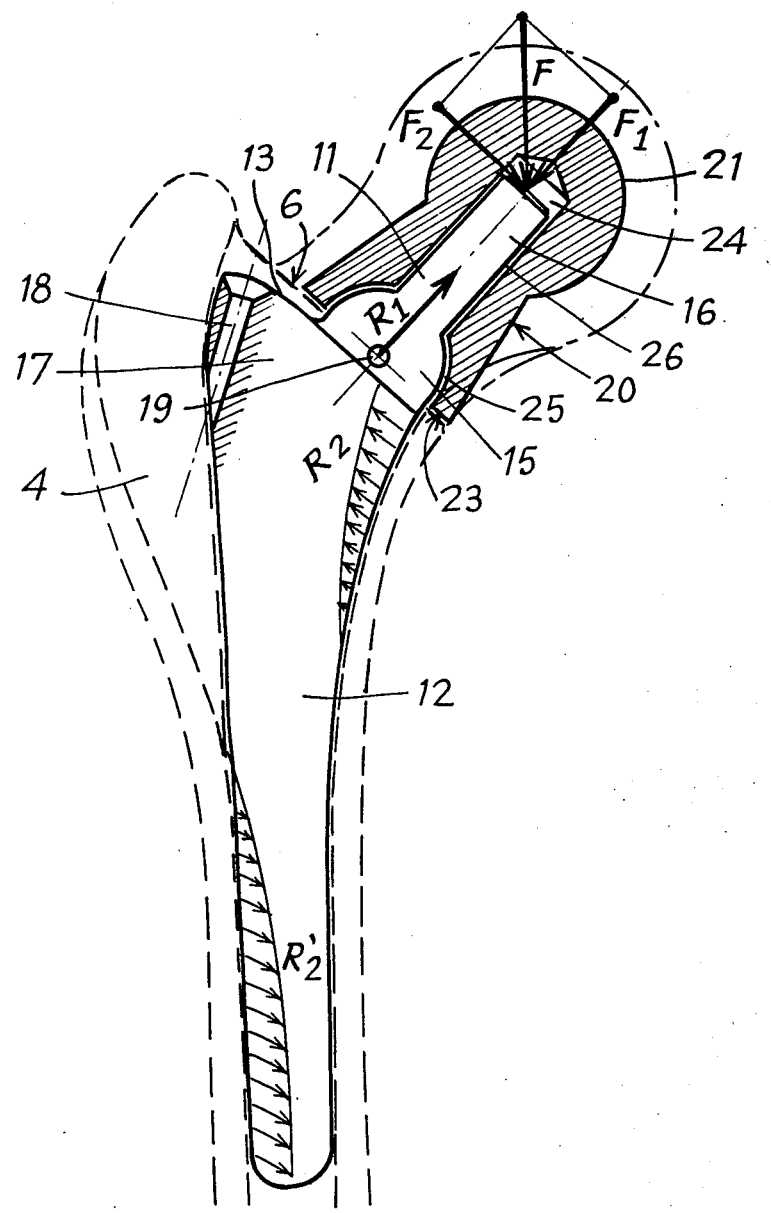

United States Patent [19]

Buttazzoni

[11] Patent Number: 4,459,708
[45] Date of Patent: Jul. 17, 1984

[54] JOINT PROSTHESIS

[76] Inventor: Bernard Buttazzoni, Le Galion 23 boulevard Augustin Cieussa, Marseille, France, 13007

[21] Appl. No.: 416,335

[22] Filed: Sep. 9, 1982

Related U.S. Application Data

[63] Continuation of Ser. No. 165,743, Jul. 3, 1980, abandoned.

[30] Foreign Application Priority Data

Jul. 10, 1979 [FR] France .................................. 79 17911

[51] Int. Cl.³ ................................................ A61F 1/04
[52] U.S. Cl. ........................................ 3/1.91; 3/1.912; 3/1.913; 128/92 C; 128/92 CA
[58] Field of Search .................. 128/92 C, 92 CA; 3/1.912, 1.913, 1.9

[56] References Cited

U.S. PATENT DOCUMENTS

| | | | |
|---|---|---|---|
| 2,682,265 | 6/1954 | Collison | 128/92 CX |
| 2,785,673 | 3/1957 | Anderson | 128/92 CA |
| 3,685,058 | 8/1972 | Tronzo | 128/92 C X |
| 3,863,273 | 2/1975 | Averill | 128/92 C X |
| 3,874,003 | 4/1975 | Moser et al. | 128/92 C |
| 4,032,994 | 7/1977 | Frey | 3/1.912 |
| 4,051,559 | 11/1977 | Pifferi | 128/92 C X |
| 4,227,265 | 10/1980 | Frey | 3/1.913 |

FOREIGN PATENT DOCUMENTS

| | | | |
|---|---|---|---|
| 2059381 | 12/1970 | Fed. Rep. of Germany | 128/92 C X |
| 1046516 | 12/1951 | France | 128/92 C |
| 2105998 | 4/1972 | France | 3/1.713 |
| 2251303 | 11/1974 | France | 128/92 C X |
| 2360292 | 7/1977 | France | 128/92 C X |
| 2413078 | 1/1978 | France | 128/92 CA |
| 1373972 | 11/1974 | United Kingdom | 3/1.913 |

Primary Examiner—Richard J. Apley
Assistant Examiner—David J. Isabella

[57] ABSTRACT

The invention relates to a joint prosthesis having an articular member fitted on an implant element housed in the bone cavity so as to slide without turning perpendicularly to the resection surface. The implant element is not provided with any abutting edge to limit its insertion into the bone cavity and the articular member is permanently supported with no twisting moment by the resection surface owing to its sliding possibility. The invention finds an application in hip joint endoprostheses.

7 Claims, 5 Drawing Figures

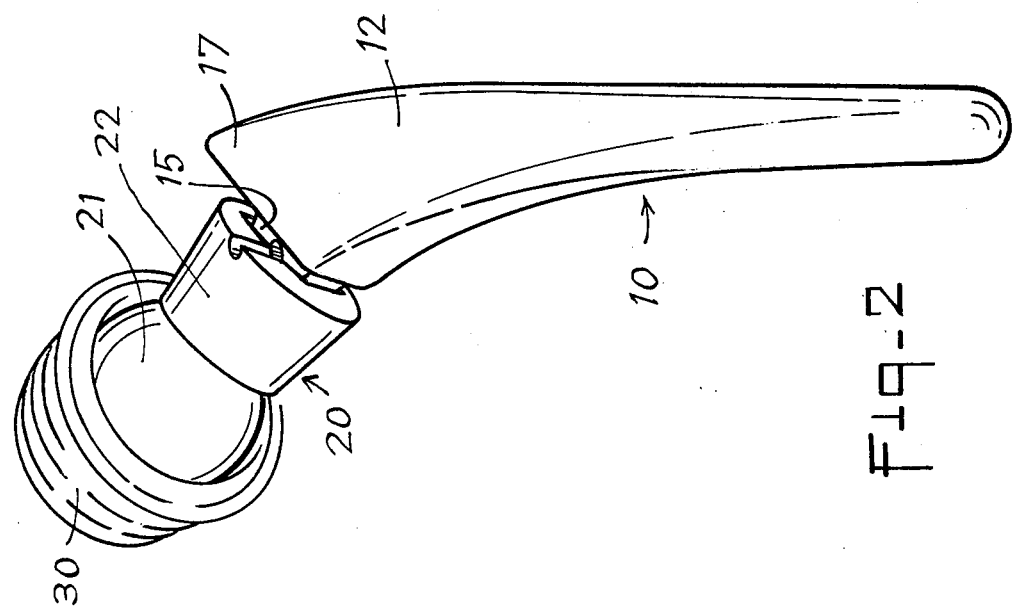
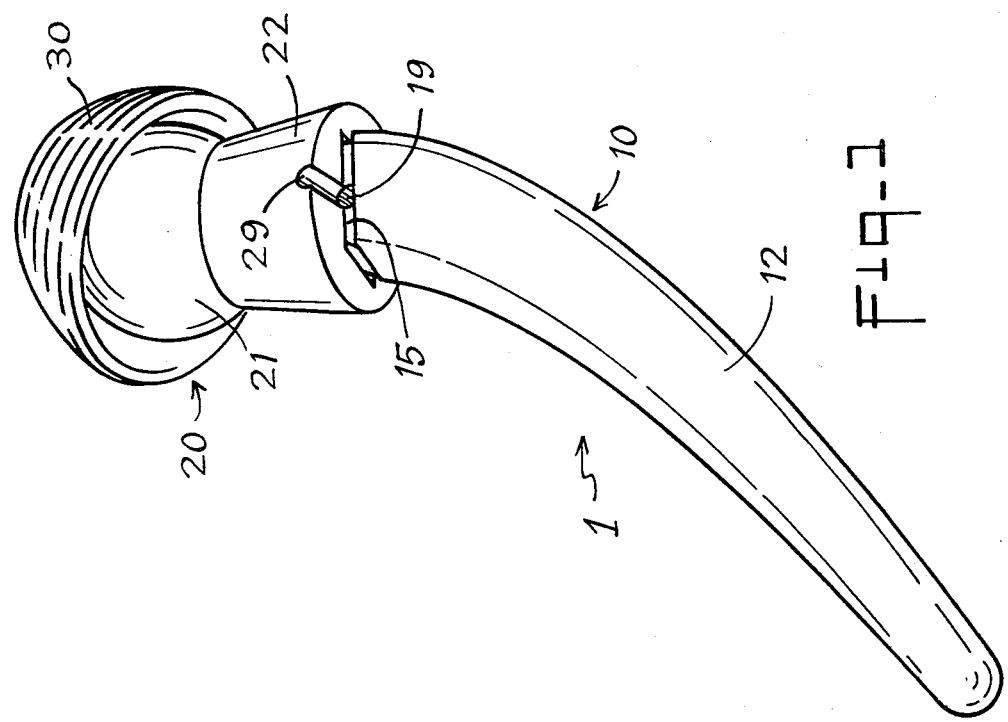

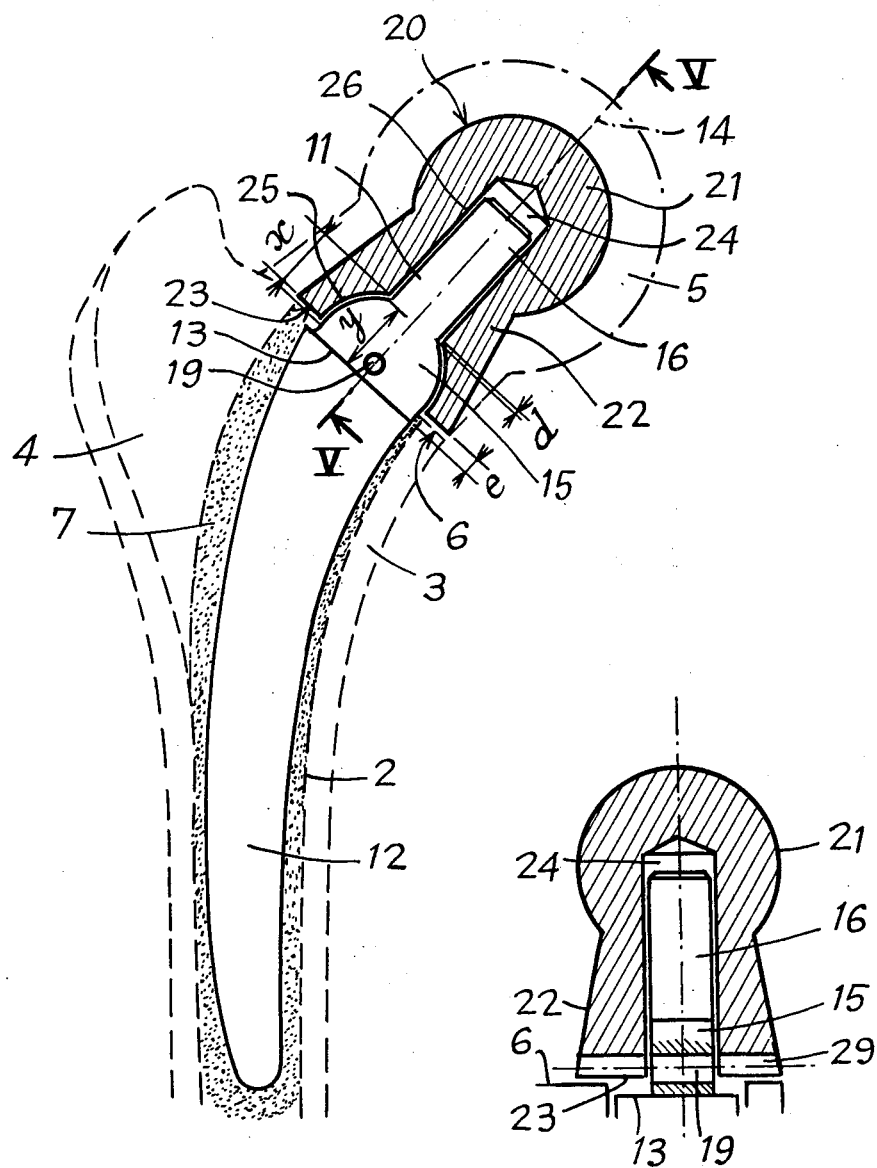

U.S. Patent  Jul. 17, 1984  Sheet 3 of 3  4,459,708

JOINT PROSTHESIS

This is a continuation of application Ser. No. 165,743, filed July 3, 1980 now abandoned.

The present invention concerns a joint prosthesis of the type comprising an implant element destined to be fitted in a cavity provided in a bone structure, and an articular element provided at one end of the implant element and showing an edge adapted to abut on the edge of the opening of the said cavity when the implant element is fitted therein.

The invention finds an application in bone surgery for restoring bone articulations and, in particular, in the domain of hip endoprostheses.

Currently known joint prostheses comprise an implant stem which is destined to be cemented or anchored inside a long bone (such as the femur) and an articular member, shaped as a spherical head for example, built-on to the implant element or in one piece therewith. The implant stem can be fixed with a bone cement or by biological anchorage with no cement. In all the known cases, an abutting edge is provided on the implant stem or, if not, on the articular element integral therewith, this in order at least to limit the insertion of the implant element into the cavity provided in the bone, the said edge abutting against the resected part of the bone which surrounds the opening of the said cavity.

A disadvantage with the known prostheses is that the support pressure of the abutting edges on the resected part is indeterminate once the implanting operation is definitely completed. Indeed there is a possibility for the support to be either total, or partial or nil. In the case of a nil or incomplete support, there is a bad transmission of the forces between the articular element and the resected part, thereby fatiguing the bone at the level of said part.

It is the object of the present invention to overcome this disadvantage and to propose a prosthesis which after anchoring or cementing of its implant element permits as faithful a reconstitution as possible of the transmission of the forces between the articular element and the resected part.

This object is reached with a prosthesis of the above-defined type, wherein, according to the invention, the implant element has no edge to limit its insertion into the bone cavity, and the articular element is mounted on the end of the implant element so as to slide without turning with respect to the latter in a direction which is parallel to, or slightly inclined with respect to the normal, to the surface containing the lower edge of the articular element, so as to allow a permanent support, with no twisting moment, of the said edge on the edge of the bone structure surrounding the cavity of the implant element after this is fitted in said cavity.

The sliding fitting with locking in rotation of the articular element on to the implant element brings many advantages.

For example, the sliding margin of the articular element ensures a constant physiological support between the articular element and the bone surface at its resected end and, if necessary, permits to make up for any deviations of the position of the implant element as well as, the latter being fixed, any displacements of the resected bone surface.

In addition, except for friction and shock-absorbing stresses, and for stresses due to the tilting and twisting couples, support pressures are transmitted directly onto the resected part without passing through the implant element. Thus there is no twisting force where the articular element is supported on the resection surface. Moreover, the implant element is no longer subjected to pounding stresses and exerts no shearing stresses in its cavity on the implant-cement interface (in the case of a cemented fixation) or on the implant-cortical interface (in the case of a biological anchorage). The absence of shearing is a factor of long life of the cemented fixation and permits a cellular re-housing in the best conditions for the biological anchorage.

Finally, the locking in rotation of the articular element onto the implant element permits to orient the contacting surfaces of the articular element and of the bone structure, according to a plane which is not exactly perpendicular to the sliding direction, which instead is slightly inclined with respect to the plane perpendicular to the sliding direction, if conditions make this preferable. By "slightly inclined" is meant here an inclination according to an angle which may vary between 0° and about 15°.

The prosthesis according to the invention can be produced from any material capable of being implanted, of supporting the mechanical stresses linked to the function of the prosthesis, and which is well accepted by the biological system in which it is implanted. Possible suitable materials known per se are, forged metal alloys, metals such as titanium, ceramics of alumina, etc.

According to the present invention, the prosthesis is advantageously produced from a composite material of the carbon-carbon type which meets the above requirements and in addition which has a modulus of elasticity approaching that of the bone. Such a material is currently used for its thermal properties, its mechanical qualities at high temperatures and for its wear characteristics (for nozzles of propellers and brake discs for example). It is produced by methods known per se which comprise the steps of preparation of a reinforcing texture and of producing a carbon matrix inside the said texture. The reinforcing texture may be single-, bi- or tridimensional; it is produced from fibres, cloths, filaments or sticks of carbon; the matrix is obtained by impregnating the texture with cokable pitch or resin followed by a pyrolysis, or by depositing carbon by a chemical vapor deposition process (by cracking of a hydrocarbon gas), or by combining both methods, the densification of the matrix requiring several successive steps.

Whenever necessary, the prosthesis according to the invention can be completed by an element intended to receive the articular element, such as for example a hemispherical cup-shaped member intended to receive the spherical head of the articular element in the particular case of a hip joint. Such additional articular element may be made of the same material as used for the rest of the prosthesis. It is also possible to use for this additional element a different material such as for example a high density polyethylene plastic material which will then also cover the articular element cooperating with this second articular element.

The invention will be more readily understood on reading the following description with reference to the accompanying drawings, in which:

FIGS. 1 and 2 are perspective views of two embodiments of a hip prosthesis according to the invention, FIGS. 3 and 4 are diagrammatical cross-sections illustrating the implantation of the prostheses respectively shown in FIGS. 1 and 2, and FIG. 5 is a partial cross-sectional diagram along line V—V of FIG. 3.

The joint prosthesis 1 shown in FIGS. 1, 3 and 5 is composed of an implant element 10, provided at one end with an endpiece 11, an articular member 20 sliding on the endpiece 11 and of a separate cup-shaped articular element 30 (shown in FIG. 1 only) which is made to receive the spherical head 21 of the member 20.

The implant element 10 comprises a stem 12 for insertion into a cavity 2 made in the diaphisis 3 of a femur 4 after resection of the natural head 5 of the femur (shown in chain-dotted lines in FIG. 3).

The endpiece 11 projects on the upper end face of the stem 12. It will be noted that the element 10 is not provided with any abutting edge limiting its insertion into the cavity 2. The edge 13 of the stem 12, where the latter joins with the endpiece 11, is slightly below and parallel to the flat upper edge 6 of the resected part, and the endpiece 11 is joined to the edge 13 inside the periphery thereof.

Said endpiece 11 is cylinder-shaped, of axis 14 perpendicular to the edges 13 and 6 and is provided, at its base with a reinforcement 15 shaped as a disc-half of which the faces are perpendicular to the edge 13. A transverse extraction bore 19 traverses the reinforcement 15 to allow the introduction therein of an axis for the purpose of extracting the stem 12 from its cavity if the need arises. Without the bore 19, the gripping of the stem 12 by its endpiece 11 only, would be difficult.

The articular member 20 comprises a truncated cone-shaped collar 22 forming skirt, the diameter of which reduces from its lower face 23 to its junction with the spherical head 21. A cavity 24 is made in the member 20 to allow the latter to slide on the endpiece 11 in parallel to the axis 14, any other relative movement between the said member 20 and the said endpiece 11 being prevented. To this effect, the cavity 24 comprises a recess which is shaped as a disc-half and cooperates with the reinforcement 15 to lock the articular member 20 in rotation about the axis 14. The recess 25 is extended by a blind hole 26 for receiving the cylindrical end 16 of the endpiece 11 so as to guide the articular member 20 in translation in parallel to the axis 14. The inside face 23 of the member 20 is perpendicular to the axis of the cavity 24 and forms the lower supporting edge of the articular member. Thus, when the member 20 is fitted in, the supporting face 23 is fully supported, with no twisting moment, on the face 6 of the resected part, in perpendicular to the sliding axis 14.

As already indicated, the locking in rotation of the articular member 20 on the implant element 10 permits to orient the supporting surface according to a plane inclined with respect to the plane perpendicular to the sliding axis 14. In practice, this possibility of inclination is limited to a relatively low value, for example less than 15°.

Two notches 29 are provided in the lower edge of the collar 22 in diametrically opposite parts so that they can be placed level with the outlet orifices of the bore 19.

The spherical head 21 forms with the cup-shaped member 30, the joint proper and transmits the forces to the bone 4.

The dimensions and outer shapes of the stem 12, of the articular member 20 and of the cup-shaped member 30, as well as the orientation with respect to the bone of the resection surface 6 and of the axis 14 are determined for example by anatomical considerations and are known. These characteristics are illustrated in the drawings and do not form part of the invention.

In the case illustrated in FIGS. 1, 3 and 5, the prosthesis 1 is fixed in the cavity 2 by way of a cement 7 (FIG. 3).

According to another embodiment of the prosthesis according to the invention (FIGS. 2 and 4), the implant element can be fixed by biological anchorage.

The prosthesis illustrated in FIGS. 2 and 4 only differs from that illustrated in FIGS. 1, 3 and 5 by the design of the stem 12 at its upper part (the corresponding elements in these two types of prostheses have in the drawings the same reference numbers).

As especially illustrated in FIG. 4, the stem 12 has a swelling at its upper part. The edge 13 is thus enlarged on one side of the element 10, thus permitting to drill a hole 18 in that edge which hole traverses the swelling 17. When the stem 12 is fitted inside the cavity 2, it can be immobilized temporarily therein by means of a screw, screwed in the bone 4 through the hole 18. When the bone re-housing along the stem 12 is completed, said screw can even be removed.

As can be seen in FIG. 4, a force applied to the spherical head 21 can be resolved into a component F1 parallel to the axis 14 and a component F2 perpendicular to said axis.

The component F1 is balanced by the reaction R1 of the resection edge 6 of the diaphysis on the edge 23 of the articular member. It is important to note that the stem 12 is fitted in so that its edge is situated at a distance e under the level of the surface 6, the distance e being between about 1 and 3 mm. Furthermore, if x designates the dimension measured in parallel to the axis 14 between the surface 23 and the junction of the recess 25 with the cylindrical bore 26 and if y designates the dimension measured in the same way between the edge 13 and the junction between the swelling 15 and the cylindrical part 16, it is important that x and y check the relation $x > y-e$. Thus, on the one hand, the total support of the edge 23 by the surface 6 does not risk to be impeded by the edge 13 even in the case of a slight subsidence of the resection surface 6 and, on the other hand, no axial force is transmitted by contact between the surface of the recess 25 and the swelling 15. The axial forces F1 are thus entirely blanced by the reaction R1. It will however be noted that a shock-absorbing function can be conferred to the fitting of the articular member on the endpiece 11, in addition to the sliding function. Thus, in case of a shock the physiological fluid imprisoned between the end of the endpiece 11 and the bottom of the cavity 24 serves as a cushion, by being forced into the diametral clearance around the endpiece 11. Part of the supporting forces can thus be transmitted to the stem in the case of a violent shock applied to the joint, as the member 20 can come to the extreme limit in abutment on the swelling 15.

The component F2 creates a tilting moment balanced by a series of reactions R2, R'2 distributed along the stem 12.

As indicated hereinabove, it will be possible to use a carbon-carbon composite material to produce the different elements of the prosthesis, and in particular a material constituted by a fibrous carbon reinforcement bonded through by a carbon matrix. By way of example, a prosthesis according to the invention was produced as follows.

The material constituting the implant element 10 was produced from stacked up layers of carbon cloth whose fibres are bonded together by infiltration to the heart of pyrocarbon, using a chemical vapor deposition process, i.e. by cracking a gaseous hydrocarbon, in the conventional way. The operation takes place in an oven at over 1000° C. and in vacuum. The preform is densified, starting from a dry carcass having a density equal to approximately 0.8 until a composite of density equal to about 1.8 is obtained. This densification is produced in several cycles of infiltration-scarifying, the scarifying consisting in removing the peripheral part of the product in order to facilitate the gaseous penetration to the heart during the following infiltration and to bring the product close to its final form. Once the densification completed, the implant element is machined to the desired shape. The final treatment to the heart with deposit of pyrocarbon gives on the surface a film of pyrocarbon which confers a good resistance to wear and to any attack from the physiological medium whilst ensuring a biological compatibility with the surrounding tissues.

Another embodiment can be adopted for the articular member 20 and for the cup-shaped member 30. The material in this case is produced from a structure constituted by an interlacement of rigidified sticks of carbon fibres constituting four bundles oriented in parallel to four large diagonals of a cube (a material such as this being described in French Pat. No. 2 276 916). The resulting structure is densified in the same conditions as the material of the implant element after having possibly reduced the porosity beforehand (for example by depositing a carbon filler.) the articular member 20 and the cup-shaped member 30 are machined from the mass of the densified block. Ceramic in the form of silicon carbide is introduced in gaseous phase in the porosity to the core of the articular member and of the cup-shaped member, at least in their contacting articular parts, until saturation of a homogeneous layer of between 10 and 500 $\mu$m thickness. A material with a carbon reinforcement structure and silicon carbide matrix is described in French Pat. No. 2 401 888. A grinding in of opposite spherical parts is effected with the techniques used for polishing fritted ceramics.

The fitting of the prosthesis is completed by adjusting the sliding play of the spherical head on the corresponding endpiece of the stem.

The invention is not limited to the description given hereinabove and modifications can of course be brought thereto without departing from the scope of protection defined in the accompanying claims.

What is claimed is:

1. A joint prosthesis comprising:
   (a) an implant element having a collarless stem for fitting rigidly into a cavity provided in a bone structure, and an end piece which projects from an end face of said implant stem, said collarless stem having no edge for limiting its insertion into said cavity in order to allow the positioning of said implant stem with said end face recessed into said cavity;
   (b) an articular member formed in one piece and having a housing therein for active sliding engagement with said end piece, said articular member having an abutting edge adapted for direct abutment against a resected surface of the bone structure surrounding said cavity;
   (c) said articular member being mounted on said end piece for continual sliding with respect thereto in each direction along an axis substantially parallel to the perpendicular from a surface including said abutting edge, said axis having an inclination in the range of about 0° to about 15° with respect to said perpendicular; and
   (d) locking means for preventing said articular member from rotating with respect to said implant stem about said axis whereby a permanent physiological support with no twisting moment is provided for said abutting edge against the supporting edge when the prosthesis is in use, thereby avoiding the transmission of axial compression forces from the articular member to the bone structure through said implant stem.

2. The joint prosthesis as claimed in claim 1, wherein said locking means comprises an enlarged reinforcement part being engaged in a corresponding recess of said housing for locking said articular member against rotation about said axis.

3. A joint prosthesis as claimed in claim 1, wherein a hole for a fixing member is provided in the implant stem and opens in the end face from whence said end piece projects.

4. The joint prosthesis as claimed in claim 1, wherein a hole through said end piece extends substantially parallel to said supporting edge.

5. The joint prosthesis as claimed in claim 1, wherein at least one of the constitutive elements is a composite material comprising a fibrous carbon reinforcement bonded therethrough by a carbon matrix.

6. A joint prosthesis as claimed in claim 1, wherein said implant element is made of a carbon-carbon composite material constituted by a carbon reinforcing structure densified to the core with pyrolytic carbon.

7. A joint prosthesis as claimed in claim 1, wherein said articular member is made of a carbon-ceramics composite material constituted by a carbon reinforcing structure densified to the core with ceramics.

* * * * *

UNITED STATES PATENT AND TRADEMARK OFFICE
CERTIFICATE OF CORRECTION

PATENT NO. : 4,459,708

DATED : July 17, 1984

INVENTOR(S) : Bernard Buttazzoni

It is certified that error appears in the above-identified patent and that said Letters Patent are hereby corrected as shown below:

Front page, first column, after the line "Inventor", insert the following:

[73] Assignee: Societe Europeenne de Propulsion, Puteaux, France

Column 5, line 4, change "pyrocarbon" to --pyrolytic carbon--.

Column 5, line 18, change "pyrocarbon" (first instance) to --pyrolytic carbon--.

Signed and Sealed this

Twenty-third Day of July 1985

[SEAL]

Attest:

DONALD J. QUIGG

Attesting Officer

Acting Commissioner of Patents and Trademarks